United States Patent
Old

(10) Patent No.: US 8,198,315 B2
(45) Date of Patent: Jun. 12, 2012

(54) THERAPEUTIC SUBSTITUTED CYCLIC LACTAMS

(75) Inventor: David W. Old, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 67 days.

(21) Appl. No.: 12/600,723

(22) PCT Filed: May 19, 2008

(86) PCT No.: PCT/US2008/064073
§ 371 (c)(1), (2), (4) Date: Nov. 18, 2009

(87) PCT Pub. No.: WO2008/144623
PCT Pub. Date: Nov. 27, 2008

(65) Prior Publication Data
US 2010/0160407 A1    Jun. 24, 2010

Related U.S. Application Data

(60) Provisional application No. 60/939,773, filed on May 23, 2007.

(51) Int. Cl.
*A61K 31/38* (2006.01)
*A61K 31/41* (2006.01)
*C07D 209/00* (2006.01)
*C07D 333/10* (2006.01)

(52) U.S. Cl. ........ 514/422; 514/448; 548/250; 548/527; 549/71

(58) Field of Classification Search .................. 514/422; 548/527
See application file for complete search history.

(56) References Cited

U.S. PATENT DOCUMENTS

| | | | |
|---|---|---|---|
| 4,539,152 A | 9/1985 | Hashimoto et al. | |
| 6,552,067 B2 | 4/2003 | Cameron et al. | |
| 7,091,231 B2 | 8/2006 | Donde | |
| 7,592,366 B2 * | 9/2009 | Old et al. | 514/448 |
| 2005/0176800 A1 | 8/2005 | Liao et al. | |
| 2006/0205800 A1 | 9/2006 | Donde | |
| 2006/0252742 A1 | 11/2006 | Old et al. | |
| 2009/0186866 A1 | 7/2009 | Old et al. | |
| 2010/0292293 A1 * | 11/2010 | Old et al. | 514/422 |

FOREIGN PATENT DOCUMENTS

WO  WO 2006/061366  6/2006
WO  WO 2006/098918  9/2006

OTHER PUBLICATIONS

NIH Report on Glaucoma, printed Jun. 21, 2011.*
U.S. Appl. No. 11/553,143, filed Oct. 26, 2006, Yariv Donde.
Richard B. Silverman "Prodrugs and Drug Delivery Systems,", Organic Chemistry of Drug Design and Drug Action, 2d Ed., Elsevier Academic Press: Amsterdam, 2004, pp. 496-557.
Tani, et al. Bioorg. Med. Chem. Lett. 2002, 10, 1093-1106.
Kabashima et al, "The prostaglandin receptor EP4 suppresses colitis, mucosal damage and CD4 cell activation in the gut", The Journal of Clinical Investigation, Apr. 2002, vol. 109, No. 7, pp. 883-893.
Depres et al, "Synthesis of Ring Modified Prostaglandins" Tetrahedron vol. 37, pp. 621-628, 1981.
Depres et al, "β-Lactam Prostaglandins", Tetrahedron Letters No. 25, pp. 2191-2194, 1978.

* cited by examiner

*Primary Examiner* — Susannah Chung
(74) *Attorney, Agent, or Firm* — Kevin J. Forrestal; John E. Wurst; Doina G. Ene

(57) ABSTRACT

Disclosed and described herein is a compound having a formula (I) therapeutic methods, medicaments, and compositions related thereto are also disclosed.

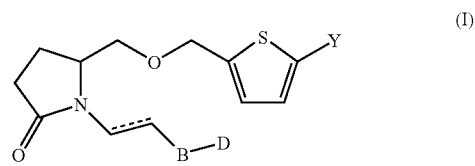

(I)

10 Claims, No Drawings

THERAPEUTIC SUBSTITUTED CYCLIC LACTAMS

CROSS REFERENCE

This is a national stage application under 35 U.S.C. 371 of PCT patent application PCT/US08/64073, filed on May 19, 2008, which claims the benefit of U.S. Provisional Patent Application U.S. Application Ser. No. 60/939,773, filed May 23, 2007, each of which is hereby incorporated by reference in its entirety.

DESCRIPTION OF THE INVENTION

Disclosed and described herein is a compound having a formula

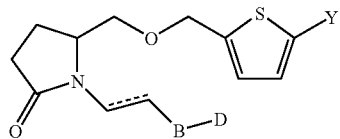

wherein a dashed line indicates the presence or absence of a covalent bond;
Y is an organic acid functional group, or an amide or ester thereof comprising up to 14 carbon atoms; or Y is hydroxymethyl or an ether thereof comprising up to 14 carbon atoms; or Y is a tetrazolyl functional group;

B is —CH(OH)—, —C(=O)—, —CH$_2$CH(OH)—, or —CH$_2$C(=O)—; and
D is alkyl, aryl, heteroaryl, arylalkyl, or heteroarylalkyl.

These compounds are useful for reducing intraocular pressure or treating glaucoma.

One embodiment is a method of treating glaucoma comprising administering a compound disclosed herein.

Another embodiment is a method of reducing intraocular pressure comprising administering a compound disclosed herein.

Another embodiment is use of a compound disclosed herein in the manufacture of a medicament for the reduction of intraocular pressure.

Another embodiment is use of a compound disclosed herein in the manufacture of a medicament for the treatment of glaucoma.

For the purposes of this disclosure, "treat," "treating," or "treatment" refer to the use of a compound, composition, therapeutically active agent, or drug in the diagnosis, cure, mitigation, treatment, prevention of disease or other undesirable condition.

Unless otherwise indicated, reference to a compound should be construed broadly to include pharmaceutically acceptable salts, prodrugs, tautomers, alternate solid forms, and non-covalent complexes of a chemical entity of the depicted structure or chemical name.

A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt is a chemical species having an ionic form of the compound, such as a conjugate acid or base, associated with a corresponding amount of counter-ions. Salts can form from or incorporate one or more deprotonated acidic groups (e.g. carboxylic acids), one or more protonated basic groups (e.g. amines), or both (e.g. zwitterions).

A prodrug is a compound which is converted to a therapeutically active compound after administration. While not intending to limit the scope of the invention, conversion may occur by hydrolysis of an ester group or some other biologically labile group. Generally, but not necessarily, a prodrug is inactive or less active than the therapeutically active compound to which it is converted. Prodrug preparation is well known in the art. For example, "Prodrugs and Drug Delivery Systems," which is a chapter in Richard B. Silverman, *Organic Chemistry of Drug Design and Drug Action*, 2d Ed., Elsevier Academic Press: Amsterdam, 2004, pp. 496-557, provides further detail on the subject.

Tautomers are isomers that are in rapid equilibrium with one another. They often, but do not necessarily, include a transfer of a proton, hydrogen atom, or hydride ion. For example, the structures herein are intended to include, but are not limited to, the tautomeric forms shown below.

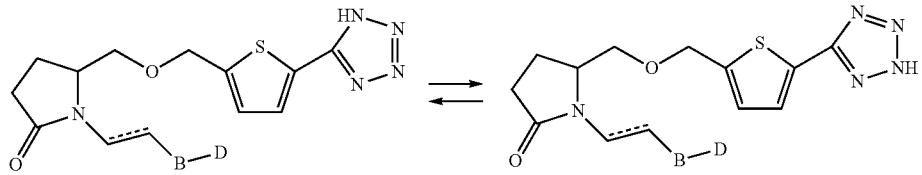

Unless stereochemistry is explicitly depicted, a structure is intended to include every possible stereoisomer, both pure or in any possible mixture.

Alternate solid forms are different solid forms than those that may result from practicing the procedures described herein. For example, alternate solid forms may be polymorphs, different kinds of amorphous solid forms, glasses, and the like.

Non-covalent complexes are complexes that may form between the compound and one or more additional chemical species that do not involve a covalent bonding interaction between the compound and the additional chemical species. They may or may not have a specific ratio between the compound and the additional chemical species. Examples might include solvates, hydrates, charge transfer complexes, and the like.

Hydrocarbyl is a moiety consisting of carbon and hydrogen only, including, but not limited to:
  a. alkyl, meaning hydrocarbyl having no double or triple bonds, including, but not limited to:
    linear alkyl, e.g. methyl, ethyl, n-propyl, n-butyl, n-pentyl, n-hexyl, etc.,
    branched alkyl, e.g. iso-propyl, t-butyl and other branched butyl isomers, branched pentyl isomers, etc., cycloalkyl, e.g. cyclopropyl, cyclobutyl, cyclopentyl, cyclohexyl, etc.,
combinations of linear, branched, and/or cycloalkyl;
b. alkenyl, e.g. hydrocarbyl having 1 or more double bonds, including linear, branched, or cycloalkenyl
c. alkynyl, e.g. hydrocarbyl having 1 or more triple bonds, including linear, branched, or cycloalkenyl;
d. combinations of alkyl, alkenyl, and/or akynyl Use of the notation "$C_{x-y}$" means the moiety has from x to y carbon atoms. For example, $C_{1-6}$ alkyl means alkyl having from 1 to 6 carbon atoms, or $C_{1-6}$ hydrocarbyl means hydrocarbyl having from 1 to 6 carbon atoms.

As used herein, "aryl" is phenyl, naphthyl, or biphenyl which may be substituted or unsubstituted. "Heteroaryl" is monocyclic or bicyclic heteroaryl, i.e. a monocyclic aryl ring wherein at least one nitrogen, oxygen, or sulfur atom is in the ring, or a bicyclic aromatic ring system wherein at least one nitrogen, oxygen, or sulfur atom is in at least one of the rings. Examples of heteroaryl include pyridinyl, furyl, thienyl, benzothienyl, benzofuryl, quinolinyl, imidazolyl, thiazolyl, oxazolyl, and the like.

Aryl or heteroaryl may be substituted or unsubstituted. If aryl is substituted, it may have from 1 to 5 substituents. Each substituent independently consists of from 0 to 8 carbon atoms, from 0 to 3 oxygen atoms, from 0 to 2 sulfur atoms, from 0 to 2 nitrogen atoms, from 0 to 3 fluorine atoms, from 0 to 2 chlorine atoms, from 0 to 1 bromine atoms, from 0 to 1 iodine atoms, and from 0 to 17 hydrogen atoms.

Subject to the constraints described herein (e.g. limits on the number of atoms for a substituent), examples of substituents include, but are not limited to:

hydrocarbyl, e.g. alkyl, alkenyl, alkynyl, phenyl, and the like;
hydroxyalkyl, i.e. alkyl-OH, such as hydroxymethyl, hydroxyethyl, and the like;
ether substituents, including —O-alkyl, alkyl-O-alkyl, and the like;
thioether substituents, including —S-alkyl, alkyl-S-alkyl, and the like;
amine substituents, including —$NH_2$, —NH-alkyl, —N-alkyl$^1$alkyl$^2$ (i.e., alkyl$^1$ and alkyl$^2$ are the same or different, and both are attached to N), alkyl-$NH_2$, alkyl-NH-alkyl, alkyl-N-alkyl$^1$alkyl$^2$, and the like;
aminoalkyl, meaning alkyl-amine, such as aminomethyl (—$CH_2$-amine), aminoethyl, and the like;
ester substituents, including —$CO_2$-alkyl, —$CO_2$-phenyl, etc.;
other carbonyl substituents, including aldehydes; ketones, such as acyl (i.e.

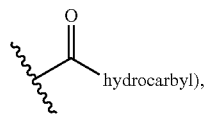

and the like; in particular, acetyl, propionyl, and benzoyl substituents are contemplated;
phenyl or substituted phenyl;
fluorocarbons or hydrofluorocarbons such as —$CF_3$, —$CH_2CF_3$, etc.; and
—CN;
combinations of the above are also possible, subject to the constraints defined;
Alternatively, a substituent may be —F, —Cl, —Br, or —I.

In particular, alkyl having from 1 to 8 carbon atoms is contemplated as a substituent.
Alternatively, alkyl having from 1 to 4 carbon atoms is contemplated;
Substituents must be sufficiently stable to be stored in a bottle at room temperature under a normal atmosphere for at least 12 hours, or stable enough to be useful for any purpose disclosed herein.

If a substituent is a salt, for example of a carboxylic acid or an amine, the counter-ion of said salt, i.e. the ion that is not covalently bonded to the remainder of the molecule is not counted for the purposes of the number of heavy atoms in a substituent. Thus, for example, the salt —$CO_2^-Na^+$ is a stable substituent consisting of 3 heavy atoms, i.e. sodium is not counted. In another example, the salt —$NH(Me)_2^+Cl^-$ is a stable substituent consisting of 3 heavy atoms, i.e. chlorine is not counted.

A dashed line indicates the presence or absence of a double bond. Thus, the structures below are contemplated.

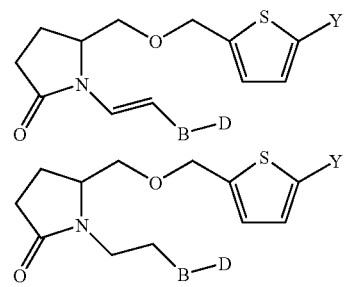

An organic acid functional group is an acidic functional group on an organic molecule. While not intending to be limiting, organic acid functional groups may comprise an oxide of carbon, sulfur, or phosphorous. Thus, while not intending to limit the scope of the invention in any way, in certain compounds Y is a carboxylic acid, sulfonic acid, or phosphonic acid functional group.

Additionally, an amide or ester of one of the organic acids mentioned above comprising up to 14 carbon atoms is also contemplated for Y. In an ester, a hydrocarbyl moiety replaces a hydrogen atom of an acid such as in a carboxylic acid ester, e.g. $CO_2Me$, $CO_2Et$, etc.

In an amide, an amine group replaces an OH of the acid. Examples of amides include $CON(R^2)_2$, $CON(OR^2)R^2$, $CON(CH_2CH_2OH)_2$, and $CONH(CH_2CH_2OH)$ where $R^2$ is independently H, $C_1$-$C_6$ alkyl, phenyl, or biphenyl. Moieties such as $CONHSO_2R^2$ are also amides of the carboxylic acid notwithstanding the fact that they may also be considered to be amides of the sulfonic acid $R^2$—$SO_3H$. The following amides are also specifically contemplated, $CONSO_2$-biphenyl, $CONSO_2$-phenyl, $CONSO_2$-heteroaryl, and $CONSO_2$-naphthyl. The biphenyl, phenyl, heteroaryl, or naphthyl may be substituted or unsubstituted.

While not intending to limit the scope of the invention in any way, Y may also be hydroxymethyl or an ether thereof comprising up to 14 carbon atoms. An ether is a functional group wherein a hydrogen of an hydroxyl is replaced by carbon, e.g., Y is $CH_2OCH_3$, $CH_2OCH_2CH_3$, etc. These groups are also bioisosteres of a carboxylic acid.

"Up to 14 carbon atoms" means that the entire Y moiety, including the carbonyl carbon of a carboxylic acid ester or amide, and both carbon atoms in the —$CH_2O$—C of an ether has 0, 1, 2, 3, 4, 5, 6, 7, 8, 9, 10, 11, 12, 13, or 14 carbon atoms.

Finally, while not intending to limit the scope of the invention in any way, Y may be a tetrazolyl functional group.

Thus, while not intending to be limiting, the structures below exemplify what is meant by tetrazolyl; carboxylic acid, phosphonic acid, sulfonic acid, and their esters and amides; hydroxymethyl and ether of hydroxymethyl. In these structures, R is H or hydrocarbyl, subject to the constraints defined herein.

Each structure below represents a specific embodiment which is individually contemplated, as well as pharmaceutically acceptable salts and prodrugs of compounds which are represented by the structures.

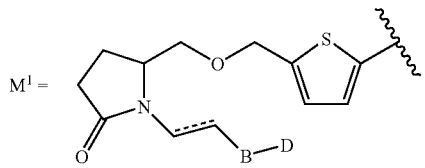

| Organic Acids | Esters | Amides |
|---|---|---|
| $M^1$—$CO_2H$ | $M^1$—$CO_2R$ | $M^1$—$CO_2NR_2$ |
| Carboxylic Acid | Carboxylic Acid Ester | Carboxylic Acid Amide |
| $M^1$—$P(O)(OH)_2$ | $M^1$—$P(O)(OH)OR$ | $M^1$—$P(O)(OH)NR_2$ |
| Phosphonic Acid | Phosphonic Acid Ester | Phosphonic Acid Amide |
| $M^1$—$SO_3H$ | $M^1$—$SO_3R$ | $M^1$—$SO_3NR_2$ |
| Sulfonic Acid | Sulfonic Acid Ester | Sulfonic Acid Amide |
| $M^1$—$CH_2OH$ | $M^1$—$CH_2OR$ | |
| Hydroxymethyl | Ether | |

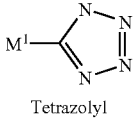

Tetrazolyl

A tetrazolyl functional group is another bioisostere of a carboxylic acid. An unsubstituted tetrazolyl functional group has two tautomeric forms, which can rapidly interconvert in aqueous or biological media, and are thus equivalent to one another.

Additionally, if $R^2$ is $C_1$-$C_6$ alkyl, phenyl, or biphenyl, other isomeric forms of the tetrazolyl functional group such as the one shown below are also possible, unsubstituted and hydrocarbyl substituted tetrazolyl up to $C_{12}$ are considered to be within the scope of the term "tetrazolyl."

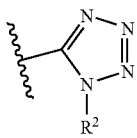

While not intending to limit the scope of the invention in any way, in one embodiment, Y is $CO_2R^2$, $CON(R^2)_2$, $CON(OR^2)R^2$, $CON(CH_2CH_2OH)_2$, $CONH(CH_2CH_2OH)$, $CH_2OH$, $P(O)(OH)_2$, $CONHSO_2R^2$, $SO_2N(R^2)_2$, $SO_2NHR^2$,

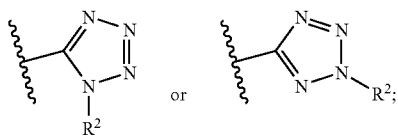

wherein $R^2$ is independently H, $C_1$-$C_6$ alkyl, unsubstituted phenyl, or unsubstituted biphenyl.

B is —CH(OH)—, —C(=O)—, —CH$_2$CH(OH)—, or —CH$_2$C(=O)—. Thus, the structures below are contemplated.

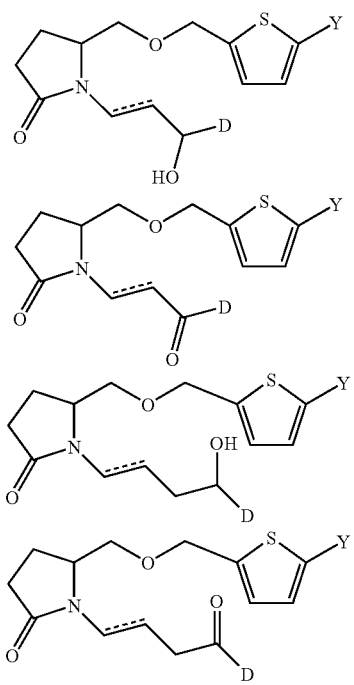

In one embodiment, D is linear alkyl having 2, 3, 4, 5, or 6 carbon atoms.

Other examples of D are depicted below.

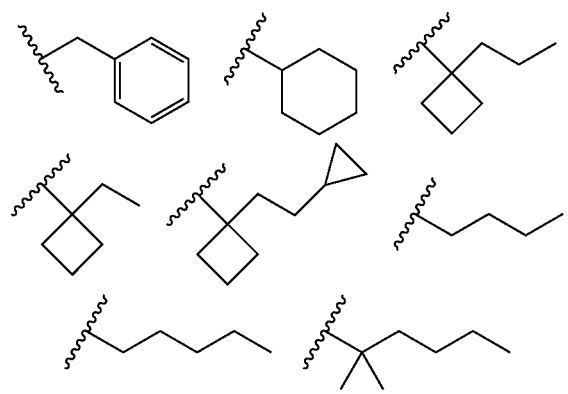

In one embodiment D is alkyl.
In another embodiment B is —CH(OH)—.
In another embodiment, the compound has the formula

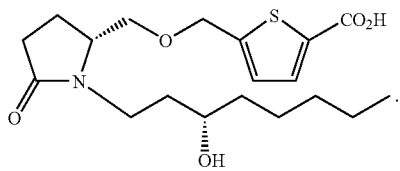

In another embodiment, the compound has the formula

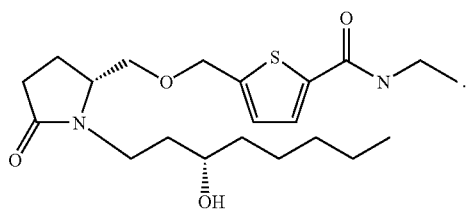

In another embodiment, the compound has the formula

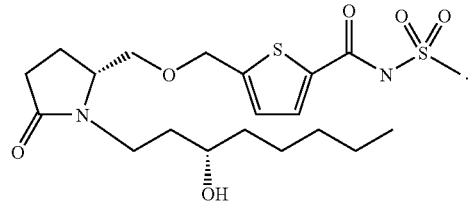

In another embodiment B is —CH$_2$CH(OH)—.
In another embodiment, the compound has the formula

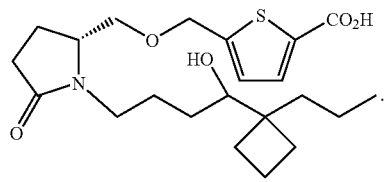

Hypothetical examples of useful compounds include those shown below.

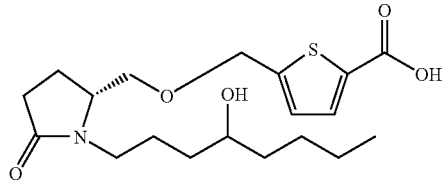

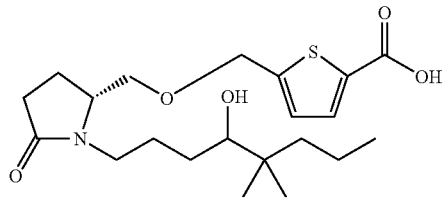

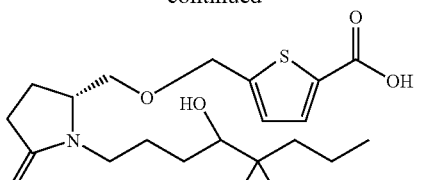

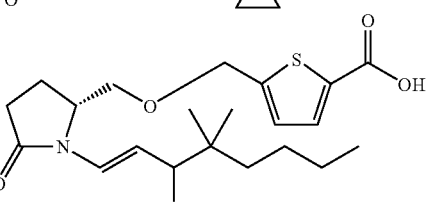

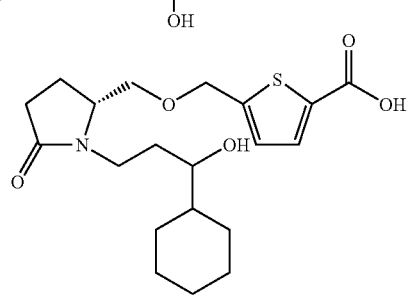

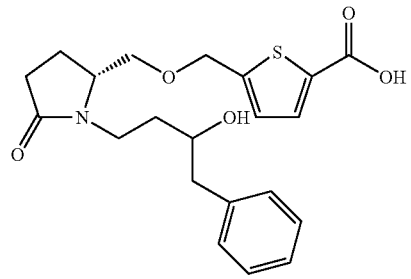

In Vitro Testing

U.S. patent application Ser. No. 11/553,143, filed on Oct. 26, 2006, incorporated by reference herein, describes the methods used to obtain the in vitro data in the table below.

| Structure | EP2 data | | | EP4 data | | Other Receptors (EC50 in nM) | | | | | |
|---|---|---|---|---|---|---|---|---|---|---|---|
| | flipr EC50 | cAMP EC50 | Ki | flip EC50 | KI | hFP | hEP1 | hEP3A | hTP | hIP | hDP |
| (structure) | 1568 | 19 | 2880 | 7846 | 8719 | NA | NA | 2223 | 4888 | NA | 6.8 |
| (structure) | NA | | | NA | | NA | NA | 2035 | >10000 | >10000 | 194 |

-continued

| Structure | EP2 data | | | EP4 data | | Other Receptors (EC50 in nM) | | | | | |
| --- | --- | --- | --- | --- | --- | --- | --- | --- | --- | --- | --- |
| | flipr EC50 | cAMP EC50 | Ki | flip EC50 | KI | hFP | hEP1 | hEP3A | hTP | hIP | hDP |
| 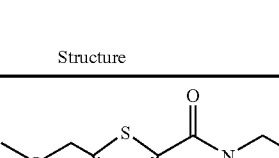 | NA | | | NA | | NA | NA | NA | >10000 | >10000 | >10000 |
| 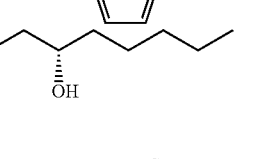 | >10000 | 20 | 1202 | NA | | NA | NA | >10000 | >10000 | >10000 | 213 |

In Vivo Testing

U.S. Pat. No. 7,091,231 describes the methods used to carry out the tests reported below.

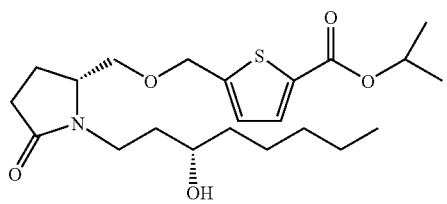

5-[(R)-1-((S)-3-Hydroxyoctyl)-5-oxopyrrolidin-2-yl-methoxymethyl]-thiophene-2-carboxylic isopropyl ester was tested in normotensive dogs at 2 concentrations, dosing once daily for 5 days. At 0.1%, the maximum intraocular pressure (TOP) decrease from baseline was 8 mmHg (47%) at 78 h; the maximum ocular surface hyperemia (OSH) score was 2.25 at 50 h. At 0.01%, the maximum TOP decrease from baseline was 6.1 mmHg (35%) at 78 h; the maximum OSH score was 1.7 at 30 h. This compound was also tested in laser-induced hypertensive monkeys, using one single day dose. At 0.1%, the maximum TOP decrease from baseline was 17 mmHg (48%) at 6 h.

Scheme 1

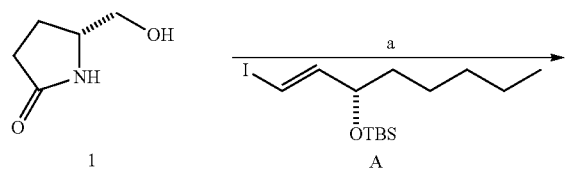

(a) CuI, MeN(H)CH₂CH₂N(H)Me, A, K₂CO₃, MeCN;
(b) Pd/C, H₂, EtOAc;
(c) NaH, B, DMF;
(d) HF-pyridine, MeCN;
(d) LiOH, H₂O, THF.

Example 1

5-[(R)-1-((S)-3-Hydroxyoctyl)-5-oxopyrrolidin-2-ylmethoxymethyl]-thiophene-2-carboxylic acid (6)

Step 1. Vinylation of 1 to Give 2

Potassium carbonate (730 mg, 5.28 mmol), copper(I) iodide (54 mg, 0.28 mmol) and N,N'-dimethylethylenediamine (29 µL, 0.27 mmol) were added sequentially to a solution of (R)-5-(hydroxymethyl)-pyrrolidin-2-one (1, Aldrich chemical, 365 mg, 3.17 mmol) and vinyl iodide A (Nissan Chemical, 972 mg, 2.64 mmol) in MeCN (6 mL). The reaction flask was fitted with a reflux condenser, purged with nitrogen and heated at reflux for 18 h. The reaction mixture cooled to room temperature, diluted with EtOAc and filtered through celite, washing with excess EtOAc. The filtrate was concentrated in vacuo. The residue was suspended in EtOAc, filtered and concentrated a second time. Purification of the crude residue by flash column chromatography on 12 g of silica gel (60% EtOAc/hexane) afforded 627 mg (67%) of desired product 2.

Step 2. Hydrogenation of 2 to Give 3

Palladium on carbon (10 wt. %, 55 mg) was added to solution of alkene 2 (374 mg, 1.05 mmol) in EtOAc (11 mL). A hydrogen atmosphere was established by evacuating and refilling with hydrogen (5×) and the reaction mixture was stirred under a balloon of hydrogen for 30 min. The reaction mixture was filtered through celite, washing with EtOAc, and the filtrate was concentrated in vacuo. Purification of the resulting crude residue by flash column chromatography on 4 g of silica gel (50% EtOAc/hexane→EtOAc, gradient) afforded 298 mg (79%) desired product 3.

Step 3. Alkylation of 3 to Give 4

Sodium hydride (60% oil dispersion, 16 mg, 0.40 mmol) was added to a solution of alcohol 3 (99 mg, 0.28 mmol) DMF (0.7 mL) at 0° C. After 5 min, the reaction was allowed to warm to room temperature. After 30 min at room temperature, the mixture was cooled to −40° C. and a solution of bromide B (see U.S. Provisional Patent Application No. 60/804,680, filed on Jun. 14, 2006, 54 mg, 0.23 mmol) in DMF (0.7 mL) was added via cannula. After 2 h at −40° C., the reaction was quenched with 1.0 N HCl (10 mL) and extracted with EtOAc (3×30 mL). The combined extracts were washed with $H_2O$ (2×20 mL) and brine (20 mL), then dried ($Na_2SO_4$), filtered and concentrated in vacuo. Purification of the crude residue by flash column chromatography on 4 g of silica gel (hexane→EtOAc, gradient) afforded 83 mg (59%) of desired product 4.

Step 4. Deprotection of 4 to Give 5

HF-pyridine (0.25 mL) was added to a solution of silyl ether 4 (83 mg, 0.16 mmol) in MeCN (3.2 mL) at 0° C. in a plastic scintillation vial. After 1.5 h at 0° C., the reaction mixture was quenched with saturated aqueous $NaHCO_3$ (10 mL) and extracted with EtOAc (3×15 mL). The combined extracts were washed with brine (10 mL), then dried ($Na_2SO_4$), filtered and concentrated in vacuo. Purification of the crude residue by flash column chromatography on 4 g of silica gel (50% EtOAc/hexane→EtOAc, gradient) afforded 50 mg (78%) of alcohol 5.

Step 5. Saponification of 5 to Give 6

Aqueous lithium hydroxide (1 N, 0.63 mL, 0.63 mmol) was added to a solution of ester 5 (50 mg, 0.13 mmol) in THF (1.25 mL). After 18 h at room temperature, the solvent was removed under a stream of nitrogen, the residue was diluted with $H_2O$ (2 mL), acidified with 1.0 M HCl (2 mL) then extracted with EtOAc (3×15 mL). Combined extracts were washed with brine (10 mL), dried ($Na_2SO_4$), filtered and concentrated in vacuo to afford 44 mg (quant.) of the title compound (6).

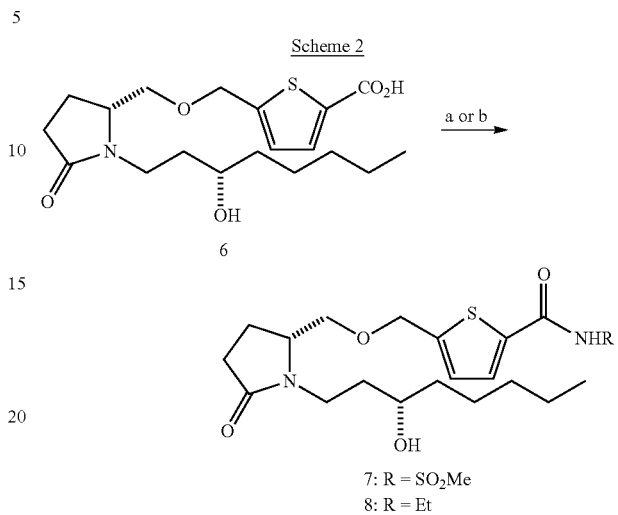

Scheme 2

7: R = $SO_2Me$
8: R = Et (a) EDCl, DMAP, $MeSO_2NH_2$, DMF;
(b) i) $ClCO_2Et$, $Et_3N$, $CH_2Cl_2$; ii) $EtNH_2$, THF.

Example 2

N-{5-[(R)-1-((S)-3-Hydroxy-octyl)-5-oxopyrrolidin-2-ylmethoxymethyl]-thiophene-2-carbonyl}-methanesulfonamide (7)

Acid 6 (12 mg, 0.031 mmol), 1-(3-dimethylaminopropyl)-3-ethylcarbodiimide hydrochloride (EDCl, 8.4 mg, 0.044 mmol), 4-dimethylaminopyridine (DMAP, 4.6 mg, 0.038 mmol) and methanesulfonamide (9 mg, 0.095 mmol) were dissolved in DMF (0.2 mL) and the resulting solution was stirred at room temperature under an atmosphere of nitrogen. After 15 h the solution was diluted with EtOAc (20 mL) and washed with 1N aqueous HCl (3×5 mL) and brine (5 mL), then dried ($Na_2SO_4$), filtered and concentrated in vacuo. Purification of the crude residue by flash column chromatography on 4 g of silica gel ($CH_2Cl_2$→10% MeOH/$CH_2Cl_2$, gradient) afforded 3.5 mg (25%) of the title compound (7).

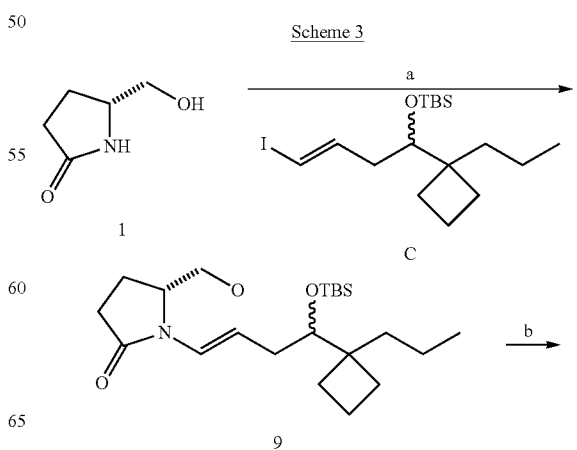

Scheme 3

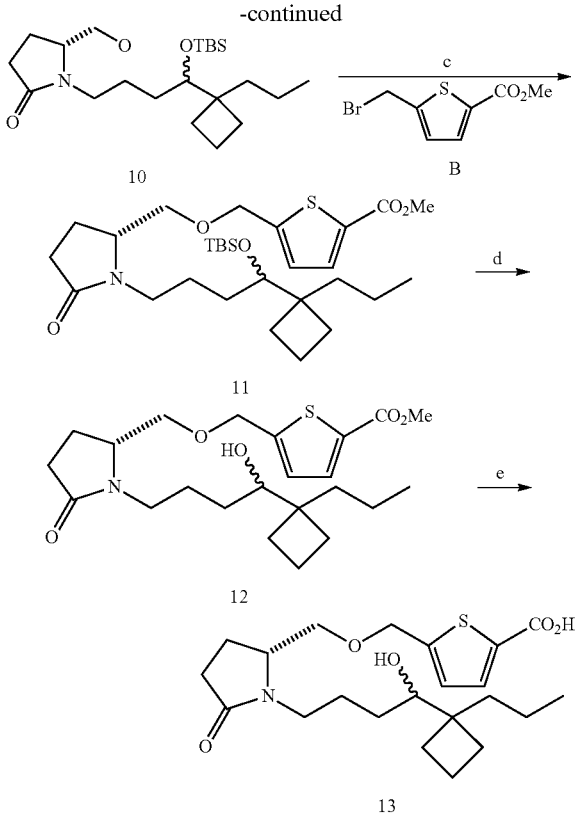

(a) CuI, MeN(H)CH₂CH₂N(H)Me, A, K₂CO₃, MeCN;
(b) Pd/C, H₂, EtOAc;
(c) NaH, B, DMSO;
(d) HF-pyridine, MeCN;
(d) LiOH, H₂O, THF.

Example 3

5-[(R)-1-((S)-3-Hydroxy-octyl)-5-oxopyrrolidin-2-ylmethoxymethyl]-thiophene-2-carboxylic acid ethylamide (8)

Triethylamine (9 mL, 0.065 mmol) and ethyl chloroformate (4.5 mL, 0.47 mmol) were added sequentially to a solution of acid 6 (12 mg, 0.031 mmol) in CH₂Cl₂ (0.2 mL) at 0° C., After 1 h at 0° C., ethylamine (2.0 M in THF, 0.15 mL, 0.30 mmol) was added and the mixture was allowed to warm to room temperature. After 18 h at room temperature, the reaction was quenched with 1.0 N HCl (5 mL) and extracted with EtOAc (3×10 mL). The combined extracts were washed with brine (5 mL), then dried (Na₂SO₄), filtered and concentrated in vacuo. Purification of the crude residue by flash column chromatography on 4 g of silica gel (CH₂Cl₂→10% MeOH/CH₂Cl₂, gradient) afforded 7.7 mg (60%) of the title compound (8).

Example 4

5-{(R)-1-[4-Hydroxy-4-(1-propylcyclobutyl)-butyl]-5-oxopyrrolidin-2-ylmethoxymethyl}-thiophene-2-carboxylic acid (13)

Step 1. Vinylation of 1 to Give 9
Potassium carbonate (474 mg, 3.43 mmol), copper(I) iodide (33 mg, 0.17 mmol) and N,N'-dimethylethylenediamine (18 µL, 0.17 mmol) were added sequentially to a solution of (R)-5-(hydroxymethyl)-pyrrolidin-2-one (1, Aldrich chemical, 237 mg, 2.06 mmol) and vinyl iodide C (see Tani, et al. Bioorg. Med. Chem. Lett. 2002, 10, 1093-1106, 700 mg, 1.71 mmol) in MeCN (3.9 mL). The reaction flask was fitted with a reflux condenser, purged with nitrogen and heated at reflux for 18 h. The reaction mixture cooled to room temperature, diluted with EtOAc and filtered through celite, washing with excess EtOAc. The filtrate was concentrated in vacuo. The residue was suspended in CH₂Cl₂, filtered and concentrated a second time. Purification of the crude residue by flash column chromatography on 40 g of silica gel (hexane→EtOAc, gradient) afforded 630 mg (93%) of desired product 9.

Step 2. Hydrogenation of 9 to Give 10
Palladium on carbon (10 wt. %, 85 mg) was added to solution of alkene 9 (630 mg, 1.59 mmol) in EtOAc (16 mL). A hydrogen atmosphere was established by evacuating and refilling with hydrogen (5×) and the reaction mixture was stirred under a balloon of hydrogen for 30 min. The reaction mixture was filtered through celite, washing with EtOAc, and the filtrate was concentrated in vacuo. Purification of the resulting crude residue by flash column chromatography on 40 g of silica gel (40% EtOAc/hexane→EtOAc, gradient) afforded 608 mg (96%) desired product 10.

Step 3. Alkylation of 10 to Give 11
Sodium hydride (60% oil dispersion, 40 mg, 1.0 mmol) was added to a solution of alcohol 10 (200 mg, 0.51 mmol) in DMSO (1.25 mL) at room temperature. After 30 min at room temperature, a solution of bromide B (130 mg, 0.55 mmol) in DMSO (1.25 mL) was added via cannula. After 15 min at room temperature, the mixture was heated at 40° C. After 16 h at 40° C., the mixture was allowed to cooled to room temperature, quenched with saturated aqueous NH₄Cl (5 mL) and 0.5 N HCl (15 mL) and extracted with EtOAc (3×40 mL). The combined extracts were washed with H₂O (2×20 mL) and brine (20 mL), then dried (Na₂SO₄), filtered and concentrated in vacuo. Purification of the crude residue by flash column chromatography on 4 g of silica gel (hexane→EtOAc, gradient) afforded 36 mg (13%) of desired product 11.

Step 4. Deprotection of 11 to Give 12
HF-pyridine (0.10 mL) was added to a solution of silyl ether 11 (35 mg, 0.06 mmol) in MeCN (1.25 mL) at 0° C. in a plastic scintillation vial. After 2 h at 0° C., the reaction mixture allowed to warm to room temperature. After 18 h at room temperature, the reaction was quenched with saturated aqueous NaHCO₃ (10 mL), extracted with EtOAc (3×15 mL). The combined extracts were washed with saturated aqueous NaHSO₃ (10 mL) and brine (10 mL) then dried (Na₂SO₄), filtered and concentrated in vacuo. Purification of the crude residue by flash column chromatography on 4 g of silica gel (40% EtOAc/hexane→EtOAc, gradient) afforded 23 mg (83%) of alcohol 12.

Step 5. Saponification of 12 to Give 13
Aqueous lithium hydroxide (1 N, 0.25 mL, 0.25 mmol) was added to a solution of ester 12 (22 mg, 0.05 mmol) in THF (0.5 mL). After 20 h at room temperature, the solvent was removed under a stream of nitrogen, the residue was diluted with H₂O (1 mL), acidified with 1.0 M HCl (2 mL) then extracted with EtOAc (3×10 mL). Combined extracts were washed with brine (5 mL), dried (Na₂SO₄), filtered and concentrated in vacuo to afford 21 mg (99%) of the title compound (13).

Example 5

5-[(R)-1-((S)-3-Hydroxyoctyl)-5-oxopyrrolidin-2-ylmethoxymethyl]-thiophene-2-carboxylic isopropyl ester DBU (9 μL, 0.06 mmol) and 2-iodopropane (62 μL, 0.62 mmol) were added to a solution of acid 6 (12 mg, 0.031 mmol) in acetone (0.3 mL) at room temperature under nitrogen. After 5 days at room temperature, the solvent was removed under a stream of nitrogen. The residue was acidified with 1 N HCl (2 mL) and extracted with EtOAc (3×10 mL). The combined extracts were washed with brine (5 mL) then dried ($Na_2SO_4$), filtered and concentrated in vacuo. Purification of the residue by flash column chromatography on silica ($CH_2Cl_2 \rightarrow 10\%$ MeOH/$CH_2Cl_2$) afforded 11.3 mg (85%) of the title compound.

What is claimed is:

1. A compound of the formula

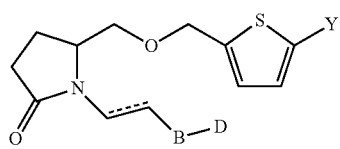

wherein a dashed line indicates the presence or absence of a covalent bond;

Y is $CO_2R^2$, $CON(R^2)_2$, $CON(OR^2)R^2$, $CON(CH_2CH_2OH)_2$, $CONH(CH_2CH_2OH)$, $CH_2OH$, $P(O)(OH)_2$, $CONHSO_2R^2$, $SO_2N(R^2)_2$, $SO_2NHR^2$,

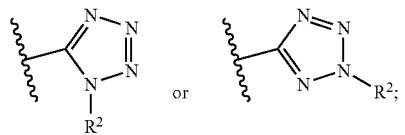

wherein $R^2$ is independently H, $C_1$-$C_6$ alkyl, unsubstituted phenyl, or unsubstituted biphenyl;

B is —CH(OH)—, —C(=O)—, —$CH_2$CH(OH)—, or —$CH_2$C(=O)—; and

D is alkyl, aryl, heteroaryl, arylalkyl, or heteroarylalkyl.

2. The compound of claim 1 wherein D is alkyl.

3. The compound of claim 2 wherein B is —CH(OH)—.

4. The compound of claim 3 of the formula

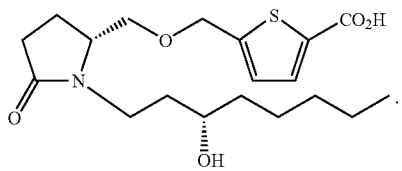

5. The compound of claim 3 of the formula

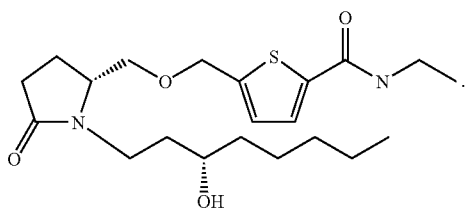

6. The compound of claim 3 of the formula

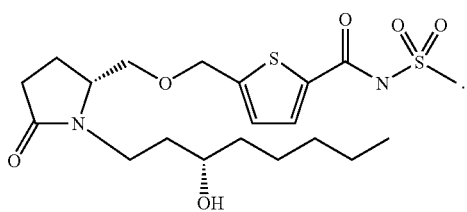

7. The compound of claim 1 wherein B is —$CH_2$CH(OH)—.

8. The compound of claim 6 of the formula

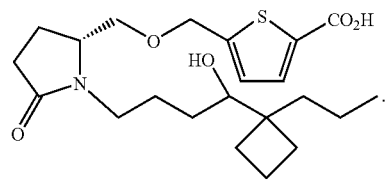

9. A method of reducing intraocular pressure comprising administering a compound according to claim 1 to a mammal in need thereof.

10. A composition comprising a compound according to claim 1, wherein said composition is a liquid suitable for topical ophthalmic administration.

* * * * *